United States Patent [19]

Robertson et al.

[11] Patent Number: 5,716,629
[45] Date of Patent: Feb. 10, 1998

[54] SYNERGISTIC BLEND OF 1-(3-CHLOROALLYL)-3,5,7-TRIAZA-1-AZONIAADAMANTANE TETRAHYDRO-3,5,-DIMETHYL-2H-1,3,5-THIADIAZINE-2-THIONE

[75] Inventors: Linda R. Robertson, St. Charles; Sasireka S. Ramesh, Aurora, both of Ill.

[73] Assignee: Nalco Chemical Company, Naperville, Ill.

[21] Appl. No.: 694,361

[22] Filed: Aug. 8, 1996

[51] Int. Cl.$^6$ .................................. A01N 25/02
[52] U.S. Cl. .................. 424/405; 514/223.8; 514/244
[58] Field of Search ......................... 424/404, 405; 514/223.8, 244, 246

[56] References Cited

U.S. PATENT DOCUMENTS 4,906,651  3/1990  Hsu ........................... 514/372

OTHER PUBLICATIONS

Mixtures of Quaternary Ammonium Compounds and Long–chain Fatty Acids as Antifungal Agents, Kull/Eisman/Sylwestrowicz/Mayer, Applied Microbiology, vol. 9, 1961, pp. 538–541.

Bergfeld et al. J. Paint Techbol. (1971) 43(563)80–91.

Primary Examiner—Neil S. Levy
Attorney, Agent, or Firm—Robert A. Miller; James J. Drake; Kelly L. Cummings

[57] ABSTRACT

The invention is a composition for controlling microbiological growth which comprises a combination of 1-(3-chloroallyl)-3,5,7-triaza-1-azoniaadamantane and tetrahydro-3,5-dimethyl-2H-1,3,5-thiadiazine-2-thione. The invention has particular utility as a composition for controlling microbiological growth in a slurry of paper machine additives such as precipitated calcium carbonate which comprises adding to said slurry a combination of 1-(3-chloroallyl)-3,5,7-triaza-1-azoniaadamantane and tetrahydro-3,5-dimethyl-2H-1,3,5-thiadiazine-2-thione.

The invention is also a method for controlling bacterial and fungal growth which comprises a combination of 1-(3-chloroallyl)-3,5,7-triaza-1-azoniaadamantane and tetrahydro-3,5-dimethyl-2H-1,3,5-thiadiazine-2-thione. The invention has particular utility as a method for controlling microbiological growth in a slurry of precipitated calcium carbonate which comprises adding to said slurry a combination of 1-(3-chloroallyl)-3,5,7-triaza-1-azoniaadamantane and tetrahydro-3,5-dimethyl-2H-1,3,5-thiadiazine-2-thione. A preferred weight ratio of adamantane to thione is from about 10:1 to about 1:10.

37 Claims, No Drawings

SYNERGISTIC BLEND OF 1-(3-CHLOROALLYL)-3,5,7-TRIAZA-1-AZONIAADAMANTANE TETRAHYDRO-3,5,-DIMETHYL-2H-1,3,5-THIADIAZINE-2-THIONE

FIELD OF THE INVENTION

The invention is a composition for controlling microbiological growth which comprises a combination of 1-(3-chloroallyl)-3,5,7-triaza-1-azoniaadamantane and tetrahydro-3,5-dimethyl-2H-1,3,5-thiadiazine-2-thione. The invention has particular utility as a composition for controlling microbiological growth in a slurry of precipitated calcium carbonate which comprises adding to said slurry a combination of 1-(3-chloroallyl)-3,5,7-triaza-1-azoniaadamantane and tetrahydro-3,5-dimethyl-2H-1,3,5-thiadiazine-2-thione.

The invention is also a method for controlling bacterial and fungal growth which comprises a combination of 1-(3-chloroallyl)-3,5,7-triaza-1-azoniaadamantane and tetrahydro-3,5-dimethyl-2H-1,3,5-thiadiazine-2-thione. The invention has particular utility as a method for controlling microbiological growth in a slurry of precipitated calcium carbonate which comprises adding to said slurry a combination of 1-(3-chloroallyl)-3,5,7-triaza-1-azoniaadamantane and tetrahydro-3,5-dimethyl-2H-1,3,5-thiadiazine-2-thione. A preferred weight ratio of adamantane to thione is from about 10:1 to about 1:10.

BACKGROUND OF THE INVENTION

Biocides and microbiocides are used to control or eliminate bacterial growth in a number of different industrial aqueous media. Often, one biocide or microbiocide is insufficient to control all bacterial growth in the aqueous medium treated. The presence of bacterial or other microorganisms interferes with the processing of industrial waters treated and may lead to corrosion and other problems with equipment that is in contact with these contaminated waters.

The mechanisms by which biocides extert antimicrobial activity depend upon the effective contact between the biocide and the microorganism and involve disruptive interaction with a biochemical or physical component of the organism, which component is essential to the organism's structure or metabolism. The targets may be an enzyme or enzymes, the cell membrane, intracellular systems, the cytoplasm, or combinations thereof, and the nature of the action is dependent on the organism, the antimicrobial agent and on the environment in which the interaction occurs.

Many broad classes of biocidal agents are known. They are commercially available for the control of microorganisms in certain sections of various industrial systems such as paints, wood, textile, paper, pulp, leather, fur, tobacco, rope, plastics, fuel, oil, cosmetics, rubber, adhesives, latex emulsions, joint cements, water treatment, laundry, and metalworking industries, among others.

One industrial system requiring control of the microorganisms is the papermaking process. Many materials are utilized in the production of paper. In addition to cellulose fibers, there are numerous materials used in the papermaking process, such as water, starch, alum, carbonates, polymers, proteins, clays, latexes or other materials used to aid in paper formation or to produce the coatings that form the printing surface.

Unfortunately, these compounds while both beneficial and necessary to the papermaking process, also support the growth of a wide variety of microorganisms, including many species of both aerobic and anaerobic bacteria, algae, nematodes, protozoa, as well as many types of fungi. The presence of these microorganisms can present serious problems to production of paper.

Microbial degradation problems in paper machines can be roughly grouped into two broad types: biofilm formation and spoilage. Each affects the quality of the finished sheet in quite a different fashion.

One result of microbial degradation is biofilm formation. This occurs because when microorganisms grow, they typically attempt to attach to a surface to form a biofilm or, in papermaker's terms, a deposit. The attachment to surfaces is a competitive advantage for microbes because they can reproduce and are not washed away with the fluids. Moreover, nutrient availability increases because of fluid flow patterns. In addition, highly varied oxygen gradients are present within the biofilms, which permits the growth of microorganisms with varied oxygen requirements. When attached, organisms are less sensitive to the effects of antimicrobial agents.

The biofilm or deposit can further increase in size as it entraps the wood fibers, carbonates, clays and other particles normally used in the papermaking process. At times, a sticky or polymeric matrix may be present. The origins of the sticky materials may include the production of exopolymeric materials by bacteria, pitch, or even upsets in the chemistry of the paper machines that would result in, for example, gelled alum. The biofilms in paper machines form massive slime deposits that can be an inch or more in thickness. It is not uncommon for long stringers, caused by filamentous bacteria, to form around fresh water showers. When these deposits break loose and fall into the paper furnish, they result in end product defects such as holes and spots or even paper sheet breaks. When this occurs, the paper with the defects must be used as broke and re-pulped or downgraded. If the paper containing these holes makes it to a new high speed coater, massive problems may result.

A second result of microbial degradation is spoilage of pulp and furnish, or chemical additives. For example, uncoated free sheet paper used for copy machines may give off an unpleasant odor when it heated as it goes through the copier. Such a problem may be traced to improperly preserved fiber chests that allow anaerobic bacteria to flourish and produce volatile fatty acids such as butyric and propionic acid. Furthermore, the anaerobic spoilage of chests may also be implicated in the formation of hazardous and explosive gases such as hydrogen and hydrogen sulfide.

Typical chemical additives adversely affected by spoilage may include starch, clay, protein, titanium dioxide, $CaCO_3$, sizers, and defoamers, among others. Each of these can potentially become microbiologically contaminated during the manufacturing process, transport or storage.

Though the economic benefits associated with the control of microbial growth on machine surfaces are understood, the problem of microbial growth in additives is often overlooked because it can be difficult to detect. Often such growth is accompanied by changes in viscosity, decreased pH values, and off-odors. Microbial contamination of additives and coatings can come from a number of sources. These may include poorly treated make-up or quench water, incoming product containing a heavy loading of spoilage microbes, and/or the heel from a previous batch or shipment. Although there are differences between the additives, there are many similarities in the way they spoil.

One papermaking additive which is susceptible to spoilage is starch, since it is an ideal food source for microbes.

Microorganisms enzymatically convert the starch components, amylose and amylopectin, into sugar for growth. Spoiled starch will not give optimum performance as either a strength additive or as a binder for coating formulations. An indication of a microbiological problem may be a drop in pH accompanied by viscosity loss.

Recycling of starch from the machine back to the run tank from a size press application can contaminate the cooked starch by bringing actively growing bacteria into a fresh food source. As the bacteria grow, they produce acidic by-products that reduce the pH. Papermakers may try to "recover" the starch by adding caustic to increase the pH. Although biocide can be added to stop further microbiological growth, the damage has been done. To eliminate a poor sizing response, the batch must be discarded.

Protein binders are often used in conjunction with other binders such as starch in coating formulations. Microorganisms can readily degrade the large protein molecules in order to utilized the amino acids for growth. A very large drop in viscosity is normally accompanied by only a slight decrease in pH. Not long after the initial pH drop, the precipitation of protein occurs. This is accompanied by the production of malodors and product discoloration.

Styrene-butadiene polymers, vinyl acetates and acrylates are synthetic binders often used in conjunction with starch and proteins. Organisms can break down the dispersing and stabilizing components in latex formulations. It is more difficult to detect this degradation since it is usually not accompanied by pH or viscosity decreases. Instead, poor adhesion of the coating to base sheet, low pigment holding capability, and undesirable supercalendering properties may be the only indicators of microbial degradation.

Among other papermaking problems caused by microbial contamination is that dye metering can be impeded due to contamination of the dye by microbes. The ensuing biofilm can cause plugging of feed lines and uneven addition of tinting dyes. However, biodegradation of papermaking tinting dyes does not seem to be a significant problem, though degradation could be a more significant problem with the azo dyes used to make colored paper grades.

Clays, precipitated and ground calcium carbonate, and titanium dioxide (which is more typically added as a brightener) are used as fillers for the sheet and as components of coatings, and are all subject to similar difficulties if microbial contamination occurs.

Unlike starch and proteins, these materials do not serve as nutrients in their own right. However, they contain dispersants that are critical to performance. If the dispersants are degraded, viscosity changes may result. Fine scratches in coating surfaces have been traced to microagglomeration the particles caused by degradation of dispersants in the fillers.

Moreover, anaerobes such as sulfate reducing bacteria can even cause a darkening of the filler and production of hydrogen sulfide. This is often seen with improperly preserved clays that must then be returned to the manufacturer for re-bleaching and treatment.

Each of the above mentioned fillers may be in a coating formulation. Spoilage of individual chemicals can impact the final formulation. The formulations present a particular challenge because carbon and nitrogen are present in ratios that enhance microbial growth. Often, the separate components are preserved with biocides that are antagonistic. When the coating components are mixed the preservatives may actually counteract each other. Furthermore, common coating practices increase the likelihood of spoilage. In a manner similar to cooked size press starch, coatings are recirculated from the machine to back to run tanks.

Microbial colonization of the paper machine may be reduced when a deposit control program is in place. Traditionally, a deposit control program has included the following items: proper housekeeping to keep surfaces free of splashed stock, anti-microbial treatment of fresh water and additives, the use of biocides to reduce microbiological growth on the machine, and scheduled boil-outs to remove the deposits that do form. This allows the mill to avoid the cost of unscheduled down time caused by sloughing of deposits and product quality loss.

The control of microbial growth in additives will produce economic benefits both in terms of optimum additive performance and in the elimination of runnability problems because good control of the machine system and enhanced quality of the finished sheet will result.

It has been discovered that combinations of a mixture of 1-(3-chloroallyl)-3,5,7-triaza-1-azoniaadamantane and tetrahydro-3,5-dimethyl-2H-1,3,5-thiadiazine-2-thione within a specified range of ratios results in synergistic biocidal activities against microorganisms in precipitated calcium carbonate. The synergy of the disruptive interaction on the organisms by the two compounds together is greater than the sum of both compounds taken alone. The synergy does not arise from an expected additivity of the components or from a predictable improvement in activity. Rather, the synergism depends largely on the interactions of the anti-microbial agents with the organism, the cellular processes of which are so complex in these interactions as to render such synergism an unpredictable and indeed, rare phenomenon. Therefore, the synergistic combination described herein does provide more effective and broader control of microorganisms in precipitated calcium carbonate than either biocide treated alone.

SUMMARY OF THE INVENTION

The invention is a composition for controlling microbiological growth which comprises a combination of 1-(3-chloroallyl)-3,5,7-triaza-1-azoniaadamantane and tetrahydro-3,5-dimethyl-2H-1,3,5-thiadiazine-2-thione. The invention has particular utility as a composition for controlling microbiological growth in a slurry of precipitated calcium carbonate which comprises adding to said slurry a combination of 1-(3-chloroallyl)-3,5,7-triaza-1-azoniaadamantane and tetrahydro-3,5-dimethyl-2H-1,3,5-thiadiazine-2-thione.

The invention is also a method for controlling bacterial and fungal growth which comprises a combination of 1-(3-chloroallyl)-3,5,7-triaza-1-azoniaadamantane and tetrahydro-3,5-dimethyl-2H-1,3,5-thiadiazine-2-thione. The invention has particular utility as a method for controlling microbiological growth in a slurry of precipitated calcium carbonate which comprises adding to said slurry a combination of 1-(3-chloroallyl)-3,5,7-triaza-1-azoniaadamantane and tetrahydro-3,5-dimethyl-2H-1,3,5-thiadiazine-2-thione. A preferred weight ratio of adamantane to thione is from about 10:1 to about 1:10.

DESCRIPTION OF THE INVENTION

The invention is a composition for controlling microbiological growth which comprises a combination of 1-(3-chloroallyl)-3,5,7-triaza-1-azoniaadamantane and tetrahydro-3,5-dimethyl-2H-1,3,5-thiadiazine-2-thione wherein the weight ratio of adamantane to thione is from about 10:1 to about 1:10.

The microbiological growth may be selected from the group consisting of algae, fungi, bacteria and combinations thereof.

The weight ratio of adamantane to thione may be from 5:1 to about 1:5. Preferably, the weight ratio of adamantane to thione may be from about 4:1. Most preferably, the weight ratio of adamantane to thione may be 3:1.

The invention is also a method for controlling bacterial and fungal growth which comprises adding to a media containing said growth a combination of 1-(3-chloroallyl)-3,5,7-triaza-1-azoniaadamantane and tetrahydro-3,5-dimethyl-2H-1,3,5-thiadiazine-2-thione wherein the weight ratio of adamantane to thione is from about 10:1 to about 1:10. The weight ratio of adamantane to thione may be from about 5:1 to about 1:5. Preferably, the weight ratio of adamantane to thione may be from about 4:1 to about 1:4. Most preferably, the weight ratio of adamantane to thione may be 3:1.

The invention is also a method of controlling bacterial growth which comprises adding to a media containing said growth a combination of 1-(3-chloroallyl)-3,5,7-triaza-1-azoniaadamantane and tetrahydro-3,5-dimethyl-2H-1,3,5-thiadiazine-2-thione wherein the weight ratio of adamantane to thione is from about 10:1 to about 1:10. The weight ratio of adamantane to thione may be from about 5:1 to about 1:5. Preferably, the weight ratio of adamantane to thione may be from about 4:1 to about 1:4. Most preferably, the weight ratio of adamantane to thione may be 3:1.

The invention is also a method of controlling fungal growth which comprises adding to a media containing said growth a combination of 1-(3-chloroallyl)-3,5,7-triaza-1-azoniaadamantane and tetrahydro-3,5-dimethyl-2H-1,3,5-thiadiazine-2-thione wherein the weight ratio of adamantane to thione is from about 10:1 to about 1:10. The weight ratio of adamantane to thione may be from about 5:1 to about 1:5. Preferably, the weight ratio of adamantane to thione may be from about 4:1 to about 1:4. Most preferably, the weight ratio of adamantane to thione may be 3:1.

The invention is also a method for controlling the growth of bacteria, algae, yeast and mold, either separately or in combination, which comprises adding to a media containing said growth a combination of 1-(3-chloroallyl)-3,5,7-triaza-1-azoniaadamantane and tetrahydro-3,5-dimethyl-2H-1,3,5-thiadiazine-2-thione wherein the weight ratio of adamantane to thione is from about 10:1 to about 1:10. The weight ratio of adamantane to thione may be from about 5:1 to about 1:5. Preferably, the weight ratio of adamantane to thione may be from about 4:1 to about 1:4. Most preferably, the weight ratio of adamantane to thione may be 3:1.

The invention is also a method of controlling bacterial and fungal growth in industrial fluids which comprises adding to a media containing said growth a combination of 1-(3-chloroallyl)-3,5,7-triaza-1-azoniaadamantane and tetrahydro-3,5-dimethyl-2H-1,3,5-thiadiazine-2-thione wherein the weight ratio of adamantane to thione from about 10:1 to about 1:10. The weight ratio of adamantane to thione may be from about 5:1 to about 1:5. Preferably, the weight ratio of adamantane to thione may be from about 4:1 to about 1:4. Most preferably, the weight ratio of adamantane to thione may be 3:1.

In the method of controlling bacterial and fungal growth, the pH of the industrial fluids may be controlled within a range of about 2.5 to about 11.0. The industrial fluids may be recirculating cooling waters. The recirculating cooling waters may have a controlled pH within the range of about 2.5 to about 9.5. Preferably, the recirculating cooling waters have a controlled pH of about 4.0 to about 7.0.

Moreover, the industrial fluids described may be used in the manufacture of paper. The industrial fluids may have a controlled pH within of about 3.5 to about 9.5. Preferably, the pH range is from about 4.5 to about 8.0.

The invention is also a method for controlling microbiological growth in a slurry selected from the group consisting of precipitated calcium carbonate and ground calcium carbonate which comprises adding to said slurry a combination of 1-(3-chloroallyl)-3,5,7-triaza-1-azoniaadamantane and tetrahydro-3,5-dimethyl-2H-1,3,5-thiadiazine-2-thione wherein the weight ratio of adamantane to thione is from about 10:1 to about 1:10. The weight ratio of adamantane to thione may be from about 5:1 to about 1:5. Preferably, the weight ratio of adamantane to thione may be from about 4:1 to about 1:4. Most preferably, the weight ratio of adamantane to thione may be 3:1. The term microbiological growth as used herein, means microorganisms selected from the group consisting of algae, fungi, bacteria and combinations thereof.

Important applications of the synergistic antimicrobial compositions of the present invention include but are not limited to: inhibiting the growth of bacteria and fungi in aqueous and organic paints, adhesives, latex emulsions, and joint cements; preserving wood; preserving cutting fluids, controlling slime-producing bacteria and fungi in pulp and papermills and cooling towers; as a spray or dip treatment for textiles and leather to prevent mold growth; protecting paint films, especially exterior paints from attack by fungi which occurs during weathering of the paint film; protecting processing equipment from slime deposits during manufacture of cane and beet sugar; preventing microorganism buildup and deposits in air washer or scrubber systems and in industrial fresh water supply systems; controlling microbial contamination and deposits in oil field drilling fluids and muds, and in secondary petroleum recovery processes; preventing bacterial and fungal growth in paper coating processes; controlling bacterial and fungal growth and deposits during the manufacture of various specialty boards, e.g., cardboard and particle board; preventing sap stain discoloration on freshly cut wood of various kinds; controlling bacterial fungal growth in clay and pigment slurries of various types; as a hard surface disinfectant to prevent growth of bacteria and fungi on walls, floors, etc.; in swimming pools to prevent algae growth; inhibiting the growth of harmful bacteria, yeast, fungi on plants, trees, fruits, seeds, or soil; protecting animal dip compositions against the buildup of microorganisms, and in photoprocessing to prevent buildup of microorganisms, and the like.

The synergistic compositions of this invention may be added separately to an industrial system or may be formulated as a simple mixture comprising its essential ingredients, or together with a suitable carrier or solvent, or an aqueous emulsion or dispersion.

The following examples are presented to describe preferred embodiments and utilities of the invention and are not meant to limit the invention unless otherwise stated in the claims appended hereto.

EXAMPLE 1

This example studied the preservative capabilities of various biocides in samples of precipitated calcium carbonate. Each biocide was tested at five different concentrations. Each test sample, containing 100 ml of a slurry of precipitated $CaCO_3$ was inoculated with a 1 ml aliquot of spoiled precipitated calcium carbonate (calcium carbonate containing microbial growth), and stirred until adequately mixed. Shortly thereafter, each sample was plated using standard microbiological serial dilution techniques to determine initial levels of bacteria and fungi.

The aerobes were plated on Difco® tryptone glucose extract agar, sulfate reducing bacteria (SRB) on a proprietary ferric citrate anaerobic medium and fungi on a modified BBL® Mycophil Agar with low pH. Aerobes plates were counted at 48 hours incubation, while the SRB and fungi were counted after 5 days. All were reported as colony forming units (cfu/ml) of slurry. The results are detailed in Table I.

TABLE I

Endpoint Determination after 1 Hour

| Biocide | Biocide Amount (ppm) | Aerobes Count (cfu/mL) | Aerobic Spores (cfu/mL) | Fungi Count (cfu/mL) |
|---|---|---|---|---|
| None | None | 8,800,000 | <100 | <100 |
| None | None | 1,100,000 | <100 | <100 |
| A | 250 | 5,000,000 | <100 | <100 |
| A | 500 | 3,400,000 | <100 | <100 |
| A | 750 | 1,500,000 | 300 | <100 |
| A | 1000 | 1,200,000 | <100 | <100 |
| A | 2000 | 790,000 | <100 | <100 |
| B | 250 | 3,200,000 | <100 | <100 |
| B | 500 | 7,100,000 | 100 | <100 |
| B | 750 | 810,000 | <100 | <100 |
| B | 1000 | 1,400,000 | <100 | <100 |
| B | 2000 | 1,200,000 | <100 | <100 |
| C | 250 | 1,300,000 | 100 | <100 |
| C | 500 | 2,400,000 | <100 | <100 |
| C | 750 | 1,300,000 | 100 | <100 |
| C | 1000 | 280,000 | <100 | <100 |
| C | 2000 | 740,000 | 600 | <100 |
| D | 250 | 880,000 | <100 | <100 |
| D | 500 | 410,000 | 100 | <100 |
| D | 750 | 530,000 | 100 | <100 |
| D | 1000 | 240,000 | <100 | <100 |
| D | 2000 | 330,000 | 100 | <100 |
| A/B | 100/100 | 2,500,000 | 100 | <100 |
| A/B | 250/250 | 3,600,000 | <100 | <100 |
| A/B | 350/350 | 6,200,000 | 200 | <100 |
| A/B | 500/500 | 5,400,000 | <100 | <100 |
| A/B | 1000/1000 | 2,900,000 | <100 | <100 |

A = tetrahydro-3,5-dimethyl-2H-1,3,5-thiadiazine-2-thione (available from Nalco Chemical Co., Naperville, IL, 24% actives)
B = 1-(3-chloroallyl)-3,5,7-triaza-1-azoniaadamantane (available from Nalco Chemical Co., Naperville, IL, 67.5% actives)
C = 2-bromo-2-nitropropane-1,3-diol (10% actives)
D = mixture of 5-chloro-2-methyl-4-isothiazolin-3-one and 2-methyl-4-isothiazolin-3-one (1.5% actives)

EXAMPLE 2

Aliquots were taken from each sample to determine colony forming units/mL of $CaCO_3$. After plating, the samples were each rechallenged with an additional/mL aliquot of spoiled material to obtain the results of Table II, which detail the presence of microorganisms in the precipitated calcium carbonate after 21 days.

TABLE II

Endpoint Determination after 21 Days

| Biocide | Biocide Amount (ppm) | Aerobes Count (cfu/mL) | Fungi Count (cfu/mL) |
|---|---|---|---|
| none | none | 2,800,000 | <100 |
| none | none | 2,500,000 | <100 |
| A | 250 | 1,600,000 | <100 |
| A | 500 | 1,400,000 | <100 |
| A | 750 | <1000 | <100 |
| A | 1000 | 2,000 | <100 |
| A | 2000 | <1000 | <100 |
| B | 250 | 2,200,000 | <100 |
| B | 500 | 1,000 | <100 |
| B | 750 | <1000 | <100 |
| B | 1000 | <1000 | <100 |
| B | 2000 | <1000 | <100 |
| C | 250 | 6,900,000 | <100 |
| C | 500 | 10,000,000 | <100 |
| C | 750 | 14,000 | <100 |
| C | 1000 | <1000 | <100 |
| C | 2000 | <1000 | <100 |
| D | 250 | 10,000,000 | <100 |
| D | 500 | 15,000,000 | <100 |
| D | 750 | 340,000 | <100 |
| D | 1000 | 200,000 | <100 |
| D | 2000 | <1000 | <100 |
| A/B | 100/100 | 1,100,000 | <100 |
| A/B | 250/250 | <1000 | <100 |
| A/B | 350/350 | <1000 | <100 |
| A/B | 500/500 | <1000 | <100 |
| A/B | 1000/1000 | 3,000 | <100 |

A = tetrahydro-3,5-dimethyl-2H-1,3,5-thiadiazine-2-thione (available from Nalco Chemical Co., Naperville, IL, 24% actives)
B = 1-(3-chloroallyl)-3,5,7-triaza-1-azoniaadamantane (available from Nalco Chemical Co., Naperville, IL, 67.5% actives)
C = 2-bromo-2-nitropropane-1,3-diol (10% actives)
D = mixture of 5-chloro-2-methyl-4-isothiazolin-3-one and 2-methyl-4-isothiazolin-3-one (1.5% actives)

EXAMPLE 3

The procedure described in Example 2 was utilized to obtain the results of Table III, which detail the presence of microbiological organisms in the precipitated calcium carbonate after 28 days.

TABLE III

Endpoint Determination after 28 Days

| Biocide | Biocide Amount (ppm) | Aerobes Count (cfu/mL) | SRB[1] (cfu/mL) | Fungi Count (cfu/mL) |
|---|---|---|---|---|
| none | none | 2,800,000 | 2200 | <10 |
| none | none | 3,000,000 | 4400 | <10 |
| A | 250 | 2,500,000 | 10 | <10 |
| A | 500 | 5,200,000 | <100 | <10 |
| A | 750 | 10,000 | <100 | <10 |
| A | 1000 | <1000 | <100 | <10 |
| A | 2000 | 1,000 | <100 | <10 |
| B | 250 | 16,000,000 | <100 | <10 |
| B | 500 | 41,000 | <100 | <10 |
| B | 750 | 8,000 | <100 | <10 |
| B | 1000 | 1,000 | <100 | <10 |
| B | 2000 | 5,000 | <100 | <10 |
| C | 250 | 7,600,000 | 11700 | <10 |
| C | 500 | 43,000,000 | >10000 | <10 |
| C | 750 | 36,000,000 | >10000 | <10 |
| C | 1000 | 20,000,000 | <100 | <10 |
| C | 2000 | <1000 | <100 | <10 |
| D | 250 | 6,300,000 | <100 | <10 |
| D | 500 | 6,800,000 | <100 | <10 |
| D | 750 | 11,000,000 | <100 | <10 |
| D | 1000 | 4,600,000 | 100 | <10 |
| D | 2000 | 10,000 | <100 | <10 |
| A/B | 100/100 | 2,500,000 | <100 | <10 |
| A/B | 250/250 | <1000 | <100 | <10 |
| A/B | 350/350 | <1000 | <100 | <10 |
| A/B | 500/500 | <1000 | <100 | <10 |
| A/B | 1000/1000 | <1000 | <100 | <10 |

A = tetrahydro-3,5-dimethyl-2H-1,3,5-thiadiazine-2-thione (available from Nalco Chemical Co., Naperville, IL, 24% actives)
B = 1-(3-chloroallyl)-3,5,7-triaza-1-azoniaadamantane (available from Nalco Chemical Co., Naperville, IL, 67.5% actives)
C = 2-bromo-2-nitropropane-1,3-diol (10% actives)
D = mixture of 5-chloro-2-methyl-4-isothiazolin-3-one and 2-methyl-4-isothiazolin-3-one (1.5% actives)
[1] = sulfate-reducing anaerobic bacteria

EXAMPLE 4

Synergism was determined by an industrially accepted method described by Kull, F. C.; Eisman, P. C.; Sylwestrowicz, H. D. and Mayer, R. L., in applied Microbiology 9:538–541 (1961) using the ratio determined by $$\frac{Qa}{Qa} + \frac{Qa}{Qb} = \text{Synergy Index } (SI)$$

wherein

QA=concentration of compound A in parts per million (ppm) acting alone, which produced an end point.

Qa=concentration of compound A in ppm, in the mixture, which produced an end point QB=concentration of compound B in ppm, acting lone, which produced an end point.

Qb=concentration of compound B in ppm, in the mixture, which produced an end point.

when the sum of Qa/QA and Qb/QB is greater than one, antagonism is indicated. When the sum is equal to one additivity is indicated, and when less than one synergism is demonstrated.

The results of Table IV were obtained by analysis of the results of Tables II and III. Since the synergy indexes calculated were less than one, the combination is synergistic. The 3:1 ratio was studied under very severe conditions, even more severe than those encountered under typical storage conditions. Such extreme conditions might arise if a significant heel of spoiled material contaminated a transfer vessel or storage vessel for example. Therefore, the combination of the instant invention has been demonstrated to protect against spoilage under both normal and severe conditions.

TABLE IV

| Ratio A:B | End point Time (days) | Synergy Index | Synergy Rating |
|---|---|---|---|
| 1:3 | 21 | 0.8 | Synergy |
| 1:3 | 28 | 0.46 | Synergy |

A = tetrahydro-3,5-dimethyl-2H-1,3,5-thiadiazine-2-thione (available from Nalco Chemical Co., Naperville, IL, 24% actives)
B = 1-(3-chloroallyl)-3,5,7-triaza-1-azoniaadamantane (available from Nalco Chemical Co., Naperville, IL, 67.5% actives)

Changes can be made in the composition, operation and arrangement of the method of the present invention described herein without departing from the concept and scope of the invention as defined in the following claims:

We claim:

1. A composition for controlling sulfate reducing bacterial, aerobic bacterial and fungal growth which comprises a combination of 1-(3-chloroallyl)-3,5,7-triaza-1-azoniaadamantane and tetrahydro-3,5-dimethyl-2H-1,3,5-thiadiazine-2-thione wherein the weight ratio of adamantane to thione is from about 10:1 to about 1:10.

2. The composition of claim 1 wherein said microbiological growth is selected from the group consisting of algae, fungi, bacteria and combinations thereof.

3. The composition of claim 1 wherein the weight ratio of adamantane to thione is from about 5:1 to about 1:5.

4. The composition of claim 1 wherein the weight ratio of adamantane to thione is from about 4:1 to about 1:4.

5. The composition of claim 1 wherein the weight ratio of adamantane to thione is 3:1.

6. A method for controlling sulfate reducing bacterial, aerobic bacterial and fungal growth, which comprises adding to a media containing said growth a combination of 1-(3-chloroallyl)-3,5,7-triaza-1-azoniaadamantane and tetrahydro-3,5-dimethyl-2H-1,3,5-thiadiazine-2-thione wherein the weight ratio of adamantane to thione is from about 10:1 to about 1:10.

7. The method of claim 6 wherein the weight ratio of adamantane to thione is from about 5:1 to about 1:5.

8. The method of claim 6 wherein the weight ratio of adamantane to thione is from about 4:1 to about 1:4.

9. The method of claim 6 wherein the weight ratio of adamantane to thione is 3:1.

10. A method of controlling sulfate reducing bacterial and aerobic bacterial growth, which comprises adding to a media containing said growth a combination of 1-(3-chloroallyl)-3,5,7-triaza-1-azoniaadamantane and tetrahydro-3,5-dimethyl-2H-1,3,5-thiadiazine-2-thione wherein the weight ratio of adamantane to thione is from about 10:1 to about 1:10.

11. The method of claim 10 wherein the weight ratio of adamantane to thione is from about 5:1 to about 1:5.

12. The method of claim 10 wherein the weight ratio of adamantane to thione is from about 4:1 to about 1:4.

13. The method of claim 10 wherein the weight ratio of adamantane to thione is 3:1.

14. A method of controlling fungal growth which comprises adding to a media containing said growth a combination of 1-(3-chloroallyl)-3,5,7-triaza-1-azoniaadamantane and tetrahydro-3,5-dimethyl-2H-1,3,5-thiadiazine-2-thione wherein the weight ratio of adamantane to thione is from about 10:1 to about 1:10.

15. The method of claim 14 wherein the weight ratio of adamantane to thione is from about 5:1 to about 1:5.

16. The method of claim 14 wherein the weight ratio of adamantane to thione is from about 4:1 to about 1:4.

17. The method of claim 14 wherein the weight ratio of adamantane to thione is 3:1.

18. A method for controlling the growth of sulfate reducing bacteria, aerobic bacteria, algae, yeast and mold, either separately or in combination, which comprises adding to a media containing said growth a combination of 1-(3-chloroallyl)-3,5,7-triaza-1-azoniaadamantane and tetrahydro-3,5-dimethyl-2H-1,3,5-thiadiazine-2-thione wherein the weight ratio of adamantane to thione is from about 10:1 to about 1:10.

19. The method of claim 18 wherein the weight ratio of adamantane to thione is from about 5:1 to about 1:5.

20. The method of claim 18 wherein the weight ratio of adamantane to thione is from about 4:1 to about 1:4.

21. The method of claim 18 wherein the weight ratio of adamantane to thione is 3:1.

22. A method of controlling sulfate reducing bacterial, aerobic bacterial and fungal growth in industrial fluids which comprises adding to a media containing said growth a combination of 1-(3-chloroallyl)-3,5,7-triaza-1-azoniaadamantane and tetrahydro-3,5-dimethyl-2H-1,3,5-thiadiazine-2-thione wherein the weight ratio of adamantane to thione is from about 10:1 to about 1:10.

23. The method of claim 22 wherein the weight ratio of adamantane to thione is from about 5:1 to about 1:5.

24. The method of claim 22 wherein the weight ratio of adamantane to thione is from about 4:1 to about 1:4.

25. The method of claim 22 wherein the weight ratio of adamantane to thione is 3:1.

26. The method of controlling bacterial and fungal growth of claim 22 which comprises controlling the pH of the industrial fluids within a range of about 2.5 to about 11.0.

27. The method of claim 22 wherein the industrial fluids are recirculating cooling waters.

28. The method of claim 27 wherein the recirculating cooling waters have a controlled pH within the range of about 2.5 to about 9.5.

29. The method of claim 27 wherein the recirculating cooling waters have a controlled pH of about 4.0 to about 7.0.

30. The method of claim 22 wherein the industrial fluids are used in the manufacture of paper.

31. The method of claim 30 wherein the industrial fluids have a controlled pH within of about 3.5 to about 9.5.

32. The method of claim 30 wherein the pH range is from about 4.5 to about 8.0.

33. A method for controlling microbiological growth in a slurry selected from the group consisting of precipitated calcium carbonate and ground calcium carbonate which comprises adding to said slurry a combination of 1-(3-chloroallyl)-3,5,7-triaza-1-azoniaadamantane and tetrahydro-3,5-dimethyl-2H-1,3,5-thiadiazine-2-thione wherein the weight ratio of adamantane to thione is from about 10:1 to about 1:10.

34. The method of claim 33 wherein the weight ratio of adamantane to thione is from about 5:1 to about 1:5.

35. The method of claim 33 wherein the weight ratio of adamantane to thione is from about 4:1 to about 1:4.

36. The method of claim 33 wherein the weight ratio of adamantane to thione is 3:1.

37. The method of claim 33 wherein said microbiological growth is selected from the group consisting of algae, fungi, sulfate-reducing bacteria, aerobic, bacteria and combinations thereof.

* * * * *